United States Patent
Miyashita

Patent Number: 5,521,269
Date of Patent: May 28, 1996

[54] SPIROPYRAN COMPOUNDS AND OPTICALLY ACTIVE SPIROPYRAN COMPOUNDS AND THEIR USE

[75] Inventor: Akira Miyashita, Ageo, Japan

[73] Assignee: Otsuka Kagaku Kabushiki Kaisha, Osaka, Japan

[21] Appl. No.: 335,756

[22] PCT Filed: Mar. 10, 1994

[86] PCT No.: PCT/JP94/00384
§ 371 Date: Nov. 14, 1994
§ 102(e) Date: Nov. 14, 1994

[87] PCT Pub. No.: WO94/20502
PCT Pub. Date: Sep. 15, 1994

[30] Foreign Application Priority Data

Mar. 11, 1993 [JP] Japan .................... 5-078977

[51] Int. Cl.$^6$ .............. C08F 126/06; C08F 124/00; C08F 128/00; C07D 487/10; C07D 491/107; C07D 495/10

[52] U.S. Cl. .............. 526/259; 526/263; 526/266; 526/284; 526/288; 548/409

[58] Field of Search .................... 526/259, 263, 526/266, 284, 288; 548/409

[56] References Cited

U.S. PATENT DOCUMENTS 5,241,027  8/1993  Miyashita .................. 526/259

FOREIGN PATENT DOCUMENTS 61-076490  4/1986  Japan .

Primary Examiner—Joseph L. Schofer
Assistant Examiner—Wu C. Cheng
Attorney, Agent, or Firm—Ronald J. Kubovcik

[57] ABSTRACT

The present invention relates to a spiropyran compound represented by the formula (1); an optically active spiropyran compound wherein an asymmetric center is introduced on a spirocarbon; and optical functional materials using these compounds,

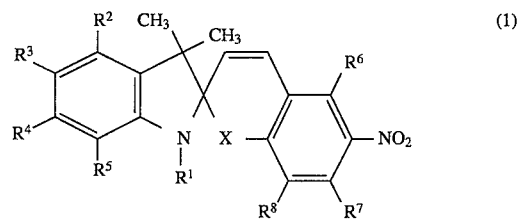

wherein $R^1$ is alkyl group having 1 to 20 carbon atoms, aralkyl group, hydroxyethyl group, methacryloxymethyl group or methacryloxyethyl group; $R^2$, $R^3$, $R^4$ and $R^5$ are the same or different and are each hydrogen atom, alkyl group having 1 to 6 carbon atoms, aryl group, aralkyl group, alkoxy group having 1 to 5 carbon atoms, hydroxymethyl group, carboxyl group, halogen atom, amino group, cyano group, trichloromethyl group, trifluoromethyl group or nitro group; $R^6$ and $R^7$ are the same or different and are each hydrogen atom, alkyl group having 1 to 6 carbon atoms, aryl group, aralkyl group, halogen atom, cyano group or nitro group; $R^6$ is alkyl group having 1 to 6 carbon atoms, hydroxymethyl group, carboxyl group, methoxycarbonyl group, methacryloxymethyl group or vinyl group; at least one of $R^1$ to $R^8$ is substituted with a substituent having properties as a reagent for optical resolution; and X is oxygen atom or sulfur atom.

9 Claims, 1 Drawing Sheet

SPIROPYRAN COMPOUNDS AND OPTICALLY ACTIVE SPIROPYRAN COMPOUNDS AND THEIR USE

TECHNICAL FIELD

The present invention relates to novel spiropyran compounds and optically active spiropyran compounds and their use. The compound of the present invention is expected for use in the fields of optical materials such as high-density optical recording materials, optical filters, image forming materials, non-linear optical devices, writable high-density optical recording materials wherein non-destructive read-out has been accomplished, photosensitive materials, non-linear optical device and conversion of optical energy into dynamic energy.

BACKGROUND ART

Spiropyran compounds are most well-known as typical organic compounds which reversibly colors or decolorizes upon exposure to the energy of light or heat. Examples and properties of these derivatives are collectively described, for example, in G. H. Brown, "Photochromism" (John Wiley & Sons, Inc., 1971). Spiropyran compounds have an asymmetric center on a spirocarbon. However, all conventional spiropyran compounds are perfect racemic modifications having an optical purity of 0%, and optically active spiropyran compounds which exhibit specific properties of optical active substances such as optical rotation have never been obtained.

The present inventors have studied intensively in order to solve the above problem of the prior art. That is, an object of the present invention is to provide spiropyran compounds and optically active spiropyran compounds and their use.

DISCLOSURE OF THE INVENTION

The present invention provides a spiropyran compound represented by the formula (1):

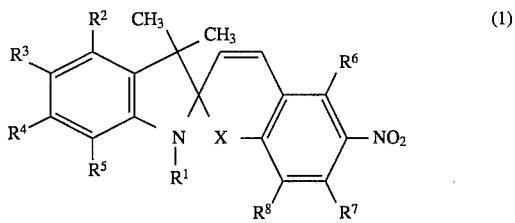

(1)

wherein $R^1$ is alkyl group having 1 to 20 carbon atoms, aralkyl group, hydroxyethyl group, methacryloxymethyl group or methacryloxyethyl group; $R^2$, $R^3$, $R^4$ and $R^5$ are the same or different and are each hydrogen atom, alkyl group having 1 to 6 carbon atoms, aryl group, aralkyl group, alkoxy group having 1 to 5 carbon atoms, hydroxymethyl group, carboxyl group, halogen atom, amino group, cyano group, trichloromethyl group, trifluoromethyl group or nitro group; $R^6$ and $R^7$ are the same or different and are each hydrogen atom, alkyl group having 1 to 6 carbon atoms, aryl group, aralkyl group, halogen atom, cyano group or nitro group; $R^8$ is alkyl group having 1 to 6 carbon atoms, hydroxymethyl group, carboxyl group, methoxycarbonyl group, methacryloxymethyl group or vinyl group; at least one of $R^1$ to $R^8$ is substituted with a substituent having properties as a reagent for optical resolution; and X is oxygen atom or sulfur atom.

The present invention also provides an optically active spiropyran compound wherein an asymmetric center is introduced on a spirocarbon, which is represented by the formula (2):

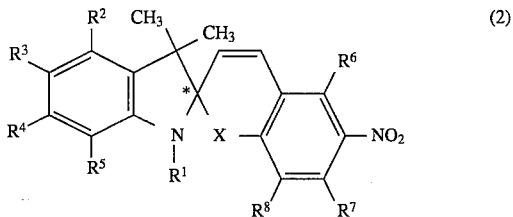

(2)

wherein $R^1$ to $R^8$ and X are the same as above.

Further, the present invention provides an optical functional material containing the spiropyran compound of the formula (1) or (2).

The spiropyran compound of the above formula (1) and the optically active spiropyran compound of the above formula (2) are compounds which are not described in literatures.

In the present specification, examples of the alkyl group having 1 to 20 carbon atoms include methyl group, ethyl group, propyl group, butyl group, hexyl group, nonyl group, dodecyl group, heptadecyl group, eicosyl group and the like. Examples of the aryl group include phenyl group, naphthyl group and the like. These groups may be substituted with substituents such as alkyl group having about 1 to 6 carbon atoms, alkoxy group having about 1 to 5 carbon atoms, halogen atom and the like. Examples of the aralkyl group include benzyl group, phenylethyl group, naphthylmethyl group and the like. The aromatic ring of these groups may be substituted with substituents such as alkyl group having about 1 to 6 carbon atoms, alkoxy group having about 1 to 5 carbon atoms, halogen atom and the like. Examples of the alkoxy group having 1 to 5 carbon atoms include methoxy group, ethoxy group, propoxy group, pentoxy group and the like. Examples of the halogen atom include fluorine atom, chlorine atom, bromine atom, iodine atom and the like.

Among compounds of the formulas (1) and (2) of the present invention, a preferred compound is a compound wherein $R^1$ is methyl group, ethyl group, propyl group, octadecyl group, hydroxyethyl group, methacryloxymethyl group or methacryloxyethyl group; $R^2$ is hydrogen atom; $R^3$ and $R^5$ are the same or different and indicate hydrogen atom, methyl group, methoxy group, chlorine atom, bromine atom, amino group, dimethylamino group, diethylamino group or nitro group; $R^4$ is hydrogen atom, methyl group or methoxy group; $R^6$ and $R^7$ indicate hydrogen atom; $R^8$ is hydrogen atom, hydroxymethyl group, carboxyl group, vinyl group or methacryloxymethyl group; at least one of $R^1$, $R^3$, $R^5$ and $R^8$ is substituted with a group having properties as a reagent for optical resolution; and X is oxygen atom or sulfur atom.

Further, the group having properties as a reagent for optical resolution may be those which are derived from known optically active substances, and examples of the optically active substance include optically active substances reacting with an alcoholic hydroxyl group, such as mandelic acid, 2-benzamidecyclohexanecarboxylic acid, 1,2-cyclohexanedicarboxylic acid, etc.; optically active substances reacting with a carboxyl group, such as α-methylbenzylamine, 1-(1-naphthyl)ethylamine, quinine, brucine, ephedrine, etc.; optically active substances reacting with an amino group, such as tartaric acid, 10-camphorsulfonic acid, phenylethanesulfonic acid, mandelic acid, malic acid, etc.

In the present invention, examples of the preferred reagent for optical resolution include (+)- and (−)-(trans)-2-benzamidecyclohexylcarboxylic acid, (+)- and (−)-(cis-2-benzamidecyclohexylcarboxylic acid, (+)- and (−)-1-phenylethanesulionic acid, (+)- and (−)-mandelic acid, (+)- and (−)-tartaric acid, (+)- and (−)-malic acid, (+)- and (−)-camphoric acid, (+)- and (−)-camphorsulfonic acid, (+)- and (−)-pyrrolidonecarboxylic acid, (+)- and (−)-aspartic acid, (+)- and (−)-α-methylbenzylamine, (+)- and (−)-1-(1-naphthyl)ethylamine, (+)- and (−)-1-phenyl-2-(p-tolyl)ethylamine, (+)- and (−)-ephedrine, (+)- and (−)-lysine, (+)- and (−)-arginine and the like.

Among compounds of the formulas (1) and (2) of the present invention, examples of the preferred compound include as followings:

8'-(trans)-benzamidecyclohexylcarbonyloxymethyl-6'-nitro-1,3,3-trimethylspiro [(2'H)-1'-benzopyran-2,2'-indoline]

8'-(trans)-benzamidecyclohexylcarbonyloxymethyl-1-isopropyl-6'-nitro-3,3-dimethylspiro [(2'H)-1'-benzopyran-2,2'-indoline]

8'-(trans)-benzamidecyclohexylcarbonyloxymethyl-1-benzyl-6'-nitro-3,3-dimethylspiro [(2'H)-1'-benzopyran-2,2'-indoline]

8'-(trans)-benzamidecyclohexylcarbonyloxymethyl-6'-nitro-1-octadecyl-3,3-dimethylspiro[(2'H)-1'-benzopyran-2,2'-indoline]

8'-(trans)-benzamidecyclohexylcarbonyloxymethyl-1-methacryloxymethyl-6'-nitro-3,3-dimethylspiro[(2'H)-1'-benzopyran-2,2'-indoline]

8'-(cis)-benzamidecyclohexylcarbonyloxymethyl-6'-nitro-1,3,3trimethylspiro[(2'H)-1'-benzopyran-2,2'-indoline]

8'-(cis)-benzamidecyclohexylcarbonyloxymethyl-1-isopropyl-6'-nitro-3,3-dimethylspiro[(2'H)-1'-benzopyran-2,2'-indoline]

8'-(cis)-benzamidecyclohexylcarbonyloxymethyl-1-benzyl-6'-nitro-3,3-dimethylspiro[(2'H)-1'-benzopyran-2,2'-indoline]

8'-(cis)-benzamidecyclohexylcarbonyloxymethyl-6'-nitro-1-octadecyl-3,3-dimethylspiro[(2'H)-]'-benzopyran-2,2'-indoline]

1-(trans)-benzamidecyclohexylcarbonyloxyethyl-6'-nitro-3,3-dimethylspiro[(2'H)-1'-benzopyran-2,2'-indoline]

1-(cis)-benzamidecyclohexylcarbonyloxyethyl-6'-nitro-3,3-dimethylspiro[(2'H)-1'-benzopyran-2,2'-indoline]

N-1-phenethyl-6'-nitro-1,3,3-trimethylspiro[(2'H)-1'-benzopyran-2,2'-indoline]-8'-carboxamide N-1-naphthylethyl-6'-nitro-1,3,3-trimethylspiro[(2'H)-1'-benzopyran-2,2'-indoline]-8'-carboxamide 5-(hydroxyphenylacetamido)-6'-nitro-1,3,3trimethylspiro [(2'H)-1'-benzopyran-2,2'-indoline]

5-(hydroxyphenylacetamido)-1-isopropyl-8'-methacryloxymethyl6'-nitro-1,3,3-trimethylspiro[(2'H)-1'-benzopyran-2,2-indoline]

5-(hydroxyphenylacetamido)-6'-nitro-1-octadecyl-3,3-dimethylspiro[(2'H)-1'-benzopyran-2,2'-indoline]

5-(hydroxyphenylacetamido)-8'-methacryloxymethyl-6'-nitro-1-octadecyl-3,3 -dimethylspiro[(2'H)-1'-benzopyran-2,2'-indoline]

6'-nitro-5-(1-phenylethanesulfonamido)-1,3,3trimethylspiro [(2'H)-1'-benzopyran-2,2'-indoline]

8'-methacryloxymethyl-6'-nitro-5-(1-phenylethanesulfonamido)- 1,3,3-trimethylspiro[(2'H)-1'-benzopyran-2,2'-indoline]

1-isopropyl-6'-nitro-5-(1-phenylethanesulfonamido)-3,3dimethylspiro[(2'H)-1'-benzopyran-2,2'-indoline]

1-benzyl-5-(1-phenylethanesulfonamido)-6'-nitro-3,3dimethylspiro[(2'H)-1'-benzopyran-2,2'-indoline]

6'-nitro-1-octadecyl-5-(1-phenylethanesulfonamido)-3,3-dimethylspiro[(2'H)-1'-benzopyran-2,2'-indoline]

8'-(trans)-benzamidecyclohexylcarbonyloxymethyl-6'-nitro-1,3,3 -trimethylspiro[(2'H)-1'-benzothiopyran-2,2'-indoline]

8'-(cis)-benzamidecyclohexylcarbonyloxymethyl-6'-nitro-1,3,3-trimethylspiro[(2'H)-1'-benzothiopyran-2,2'-indoline]

1-(trans)-benzamidecyclohexylcarbonyloxyethyl-6'-nitro-3,3-dimethylspiro[(2'H)-1'-benzothiopyran-2,2'-indoline]

N-1-phenethyl-6'-nitro-1,3,3-trimethylspiro[(2'H)-1'-benzothiopyran-2,2'-indoline]-8'-carboxamide N-1-naphthylethyl-6'-nitro-1,3,3-trimethylspiro[(2'H)-1'-benzothiopyran- 2,2'-indoline]-8'-carboxamide 5-(hydroxyphenylacetamido)-6'-nitro-1,3,3-trimethylspiro [(2'H)-1'-benzothiopyran-2,2'-indoline]

5-(hydroxyphenylacetamido)-1-isopropyl-8'-methacryloxymethyl-6'-nitro-1,3,3-trimethylspiro[(2'H)-1'-benzothiopyran-2,2'-indoline]

5-(hydroxyphenylacetamido)-6'-nitro-1-octadecyl-3,3-dimethylspiro[ (2'H)-1'-benzothiopyran-2,2'-indoline]5-(hydroxyphenylacetamido)- 8'-methacryloxymethyl-6'-nitro-1-octadecyl- 3,3-dimethylspiro[(2'H)-1'-benzothiopyran-2,2'-indoline]

6'-nitro-5-(1-phenylethanesulionamido)-1,3,3-trimethylspiro[(2'H)-1'-benzothiopyran-2,2'-indoline]

8'-methacryloxymethyl-6'-nitro-5-(1-phenylethanesulfonamido)-1,3,3 -trimethylspiro[(2'H)-1'-benzothiopyran-2,2'-indoline], etc.

The spiropyran compound of the above formula (1) of the present invention can be produced by introducing a group having properties as a reagent for optical resolution into a spiropyran compound which is produced according to a usual method. For example, it can be produced by treating 2,3,3-trimethylindolenium iodide represented by the formula (3) with a base to give a 2-methylene-3,3-dimethylindolenine derivative represented by the formula (4), condensing the resulting derivative with a 5-nitro(thio)salicylaldehyde derivative represented by the formula (5), and then introducing a group having properties as a reagent for optical resolution into the resulting condensate.

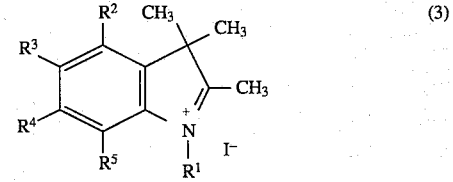

(3)

$R^1$ to $R^5$ are as defined above,

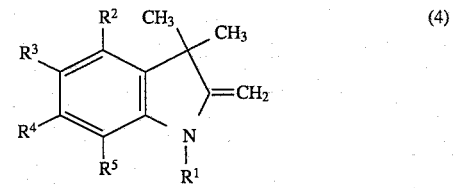

(4)

$R^1$ to $R^5$ are as defined above,

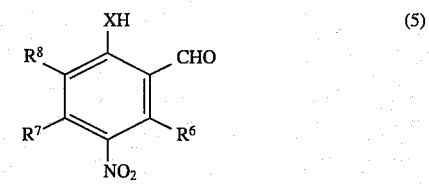

(5)

$R^6$ to $R^8$ and X are as defined above.

2,3,3-Trimethylindolenium iodide of the above formula (3) (hereinafter referred to as a "compound (3)") is, or example, a known compound described in Helv. Chim. Acta., 23, 2471 (1940), Japanese Patent Kokoku No. 58-58654, Japanese Patent Kokai No. 62-232461, Japanese Patent Kokoku No. 62-21780, Japanese Patent Kokai No. 62-21780, Japanese Patent Kokai No. 63-267783, etc., or it can be easily produced according to a method described in these literatures. Further, as the base for treating the compound (3), there can be used known bases. For example, sodium hydroxide, potassium hydroxide, etc. can be suitably used. The treatment of the compound (3) with the base is usually conducted in a solvent, for example, water, alcohols etc. can be suitably used as the solvent. The proportion of the compound (3) to the base is not specifically limited, but the base may be usually used in the equimolar amount or more to the compound.

The condensation reaction of a 2-methylene-3,3-dimethylindolenine derivative of the above formula (4) obtained by the reaction of the compound (3) with the base (hereinafter referred to as a "compound (4)") with a 5-nitro(thio)salicylaldehyde derivative of the above formula (5) (hereinafter referred to as a "compound (5)") is usually conducted in a solvent. The solvent is not specifically limited and may be any one which can dissolve the compounds (4) and (5) and is inert to the reaction. For example, methanol, ethanol, butanone, etc. can be used. The proportion of the compound (4) to the compound (5) is not specifically limited, but the compound (5) may be usually used in the equimolar amount or more to the compound (4).

Among the compound (5), a compound wherein X is sulfur atom can be produced, for example, by reacting a salicylaldehyde derivative represented by the formula (6) with N,N-dimethylthiocarbamoyl chloride according to the same manner as that described in Japanese Patent Kokai No. 60-54388 to give a 2-O-(N,N-dimethylthiocarbamoyl)benzaldehyde derivative represented by the formula (7), isomerizing the resulting derivative with heating to give a 2-S-(N,N-dimethylthiocarbamoyl)benzaldehyde derivative represented by the formula (8) and then hydrolyzing the derivative with use of alkali.

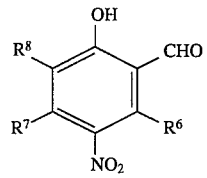

(6)

$R^6$ to $R^8$ are as defined above,

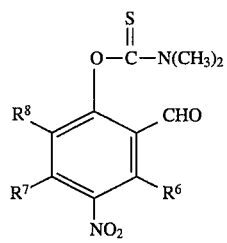

(7)

$R^6$ to $R^8$ are as defined above,

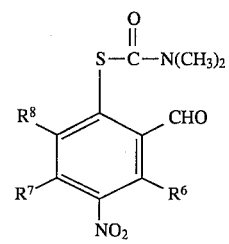

(8)

$R^6$ to $R^8$ are as defined above.

The introduction of the group having properties as a reagent for optical resolution is easily conducted by a usual organic chemical technique. The group may be introduced in the compound of the above formula (4) or (5) in advance and then condensed them, or it may be introduced into the spiropyran derivative obtained by condensing compounds of the formulas (4) and (5). The introduction of the group having properties as a reagent for optical resolution into these compounds can be accomplished by reacting these compounds with the above optically active reagent for optical resolution.

When the compounds of the formulas (4) and (5) or the condensates of the formulas (4) and (5) (hereinafter abbreviated to a "compound to be introduced") have an alcoholic functional group, optically active madelic acid, 2-benzamidecyclohexanecalboxylic acid, 1,2-cyclohexanedicarboxylic acid, etc. can preferably be introduced, respectively. When the compound to be introduced is carboxylic acid, optically active α-methylbenzylamine, 1-(1-naphthyl)ethylamine, quinine, brucine, ephedrine, etc. can be suitably introduced, respectively. When the compound to be introduced has an amino group, optically active tartaric acid, 10-camphorsulfonic acid, phenylethanesulfonic acid, mandelic acid, malic acid, etc. can be suitably introduced, respectively.

One example of a method of introducing a group derived from 2-benzamidecyclohexanecarboxylic acid as a substituent having properties as a reagent for optical resolution will be shown below.

5-Nitrosalicylaldehyde represented by the formula (9) is reacted with chloromethyl methyl ether, for example, by a method described in Japanese Patent Kokai No. 2-289580 to give 3-chloromethyl-5-nitrosalicylaldehyde represented by the formula (10).

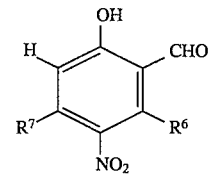

(9)

$R^6$ and $R^7$ are as defined above,

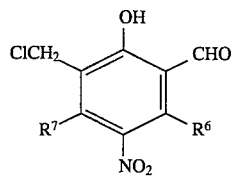

(10)

$R^6$ and $R^7$ are as defined above.

On the other hand, optically active (trans)-2-benzamidecyclohexanecarboxylic acid is once treated with ammonia and reacted with silver nitrate to give a corresponding optically active (trans)-2-benzamidecyclohexanecarboxylic acid silver salt. The resulting product is reacted with the compound represented by the above formula (10) to give optically active 3-(trans)-benzamidecyclohexylcarbonyloxymethyl- 5-nitrosalicylaldehyde represented by the formula (11).

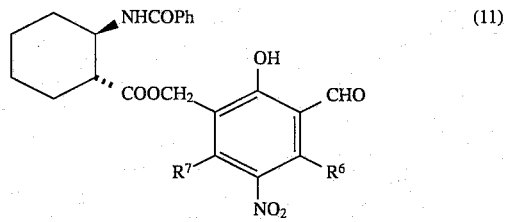

(11)

$R^6$ and $R^7$ are as defined above.

The compound of the formula (11) thus obtained can be condensed with the compound represented by the above formula (4) to give a compound represented by the formula (1) of the present invention.

The compound of the above formula (1) thus obtained is a so-called diastereomer which contains a group as a substituent having properties as a reagent for optical resolution on a spiropyran skeleton. This compound can be converted into a spiropyran compound represented by the formula (2) wherein an asymmetric center is introduced on a spirocarbon, for example, by subjecting to optical resolution by means of a so-called preferential crystallization method using a difference in solubility in a solvent or chromatography and the like, according to a method described in "Optical Active Substance" (Asakura Shoten), edited by Hiroyuki NOHIRA.

The solvent used in the preferential crystallization method may be any one which does not react with a solute and realize preferential crystallization, and is not specifically limited. For example, there can be used water, methanol, ethanol, isopropanol, butanol, ether, tetrahydrofuran, chloroform, methylene chloride, carbon tetrachloride, benzene, toluene, dimethyl sulfoxide, dimethyformamide, ethyl acetate, methyl ethyl ketone, etc. alone or in combination thereto.

When using the spiropyran compound and optically active spiropyran compound of the present invention as the optical functional material, there can be used a method which is similar to a conventional method. For example, there can be used a method comprising mixing them with a resin and molding the mixture into a suitable form such as film, sheet and the like. As the resin, there can be used a known resin and examples thereof include polymethacrylic acid, polyacrylic acid, poly($C_1$–$C_8$ alkyl ester acrylate), poly($C_1$–$C_8$ alkyl ester methacrylate), polyacrylonitrile, polyacrylamide, poly N,N-dimethylacrylamide, polyvinyl acetate, polystyrene, poly α-methylstyrene, polyvinyltoluene, polyvinyl alcohol, polyvinyl butyral, polyvinyl pyrrolidone, polyvinyl chloride, polyvinylidene chloride, polycarbonate, polyethylene oxide, nylon, polyurethane, various polyolefins, ethyl cellulose, etc. or a mixture of two or more kinds of the above. The amount of the spiropyran compound of the present invention may be selected within a wide range according to an optical function to be obtained. For example, with 100 parts by weight of resin, the amount is preferably 0.01 to 30 parts by weight, more preferably 0.1 to 10 parts by weight. Further, the molding can be conducted according to a known method. For example, in case of molding into sheet or film, there can be used a spin-coating method, spraying method, dipping method, flow-coating method, bar-coating method and the like.

Among spiropyran compounds of the present invention, those containing a polymerizable substituent can be used as the optical functional material after polymerizing itself or copolymerizing with a copolymerizable monomer to give a high polymeric spiropyran compound, followed by molding it into a suitable shape. As the copolymerizable monomer, there can be used a known monomer which is usually used. Examples thereof include methacrylic acid, acrylic acid, $C_1$–$C_8$ alkyl ester of methacrylic acid or acrylic acid, acrylonitrile, acrylic acid amide, N,N-dimethylacrylamide, vinyl acetate, styrene, α-methylstyrene, vinyltoluene and the like. They can be used singly or in combination thereof to conduct polymerization. The amount of the spiropyran compound in the copolymer may be selected within a wide range according to an optical function to be obtained. For example, the amount is preferably 0.01 to 70% by weight, more preferably about 0.7 to 30% by weight. based on the copolymer. The resulting homopolymer and copolymer can be molded according to the same manner as described above.

The compound of the present invention wherein an asymmetric center is introduced on a spirocarbon by optical resolution exhibits optical rotation in the initial stage, but is gradually epimerized at room temperature to lose its optical rotation, thereby affording a perfect epimer having an optical purity of 0%. However, when using the compound of the present invention at a solid state or in a resin matrix, its optical rotation is maintained. As is shown in examples, when the compound of the present invention is fixed in a film of a resin matrix such as polymethyl methacrylate (PMMA), deterioration of the optical rotation is observed in the initial stage of the preparation of the film. However, the tendency of deterioration of the optical rotation decreases with a lapse of time. At last, it became stable at a state wherein the optical purity is maintained at a certain level, and this state is maintained for a long period of time. Further, the optical rotation of the film can be stably measured many times without deteriorating the optical purity. As a result, by utilizing the optical rotation derived from asymmetric center on a spirocarbon of the compound of the present invention, it became possible to detect a state of the compound in a non-destructive manner using light of a wavelength which is different from light of a specific absorption wavelength of the compound.

BEST MODE OF CARRYING OUT THE INVENTION

Figure 1:
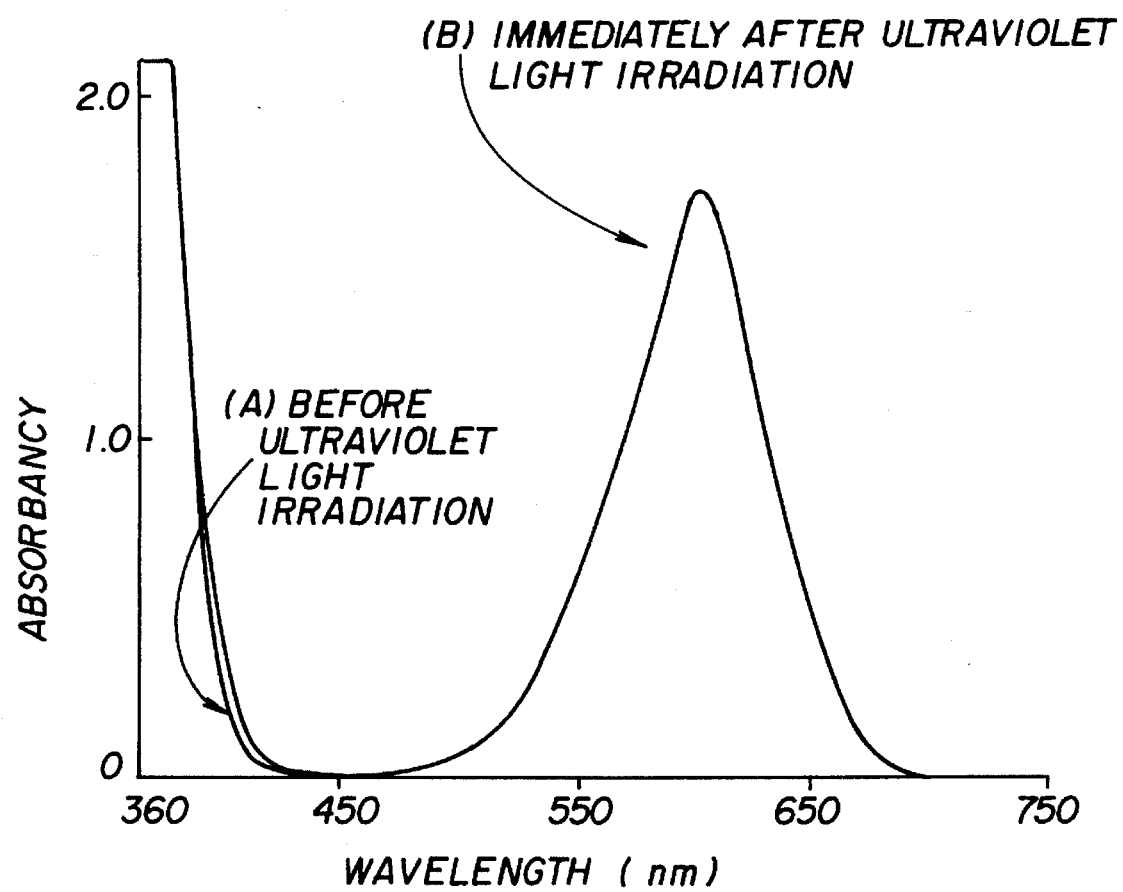
FIG. 1 is a graph illustrating an absorption spectrum measured immediately after dissolving the compound obtained in Example 6 in toluene (before ultraviolet light irradiation) and an absorption spectrum measured immediately after ultraviolet light irradiation (colored state).

The following Examples further illustrate the present invention in detail.

EXAMPLE 1

Synthesis of 3-chloromethyl-5-nitrosalicylaldehyde

5-Nitrosalicylaldehyde (2.42 g, 14.5 mmols) was suspended in 20 ml of chloromethyl methyl ether, and aluminum chloride (7.97 g, 60.0 mmols) was added while cooling in an ice bath. After stirring at room temperature for 10 minutes, the mixture was heated at 60° C. for one hour. Then, the reaction solution was poured into 100 ml of ice water while cooling in an ice bath and the resulting yellow precipitate was filtered. The resulting precipitate was recrystallized from 330 ml of hexane to give 3-chloromethyl-5-nitrosalicylaldehyde (2.49 g, 11.6 mmols) as a yellow needle-like crystal (yield 80%).

$^1$H-NMR(60 MHz, CDCl$_3$); δ 4.7(s, 2 H, —CH$_2$Cl), 8.5(s, 2 H, ArH), 10.0(s, 1H, —CHO), 12.1(s, 1 H, —OH)

EXAMPLE 2

Synthesis of (–)-(trans)-2-benzamidecyclohexanecarboxylic acid silver salt

To (–)-(trans)-2-benzamidecyclohexanecarboxylic acid (1.0 g, 4.1 mmols) was added 10 ml of distilled water and then 1 ml of 29% (by weight) ammonia water was added. After an excessive amount of ammonia was distilled off under reduced pressure, a solution prepared by dissolving silver nitrate (330 mg, 4.3 mmols) in a small amount of distilled water was added with stirring the reaction solution. The resulting white precipitate was filtered, followed by drying under reduced pressure to give (–)-(trans)-2-benzamidecyclohexanecarboxylic acid silver salt as a white solid (yield 86%).

IR(KBr, cm$^{-1}$); 2932, 1637, 1560, 1384, 1129

EXAMPLE 3

Synthesis of 3-(trans)-benzamidecyclohexyl-carbonyloxymethyl -5-nitrosalicylaldehyde 3-Chloromethyl-5-nitrosalicylaldehyde (799 mg, 3.7 mmols) was dissolved in 50 ml of benzene. To the resulting solution was added (–)-(trans)-2-benzamidecyclohexanecarboxylic acid silver salt (1.6 g, 4.5 mmols) and heated at 80° C. for 18 hours. Then, the precipitate was filtered with a gusseted filter paper and the resulting filtrate was concentrated in a rotary evaporator to give a yellow solid (1.3 g), which was recrystallized from 4 ml of 2-butanone to give 3-(trans)-benzamidecyclohexylcarbonyloxymethyl-5-nitrosalicylaldehyde (930 mg, 2.2 mmols) as a yellow crystal (yield 60° C.).

$^1$H-NMR (60 MHz, CDCl$_3$); δ 1.8 (m, 9 H, cyclohexane ring), 4.2 (br, 1 H, NH), 5.1 (s, 2 H, —CH$_2$O—), 6.0 (d, 1 H, cyclohexane ring), 7.2 (m, 5H, ArH), 8.1 (d, 2 H, ArH), 9.7 (s, 1 H, —CHO), 11.8 (br, 1 H, —OH)

EXAMPLE 4

Synthesis of 1,2,3,3-tetramethylindolenium iodide 2,3,3-Trimethylindolenine (1.7 g, 10.5 mmols) and methyl iodide (1.5 g, 10.5 mmols) were dissolved in 5 ml of chloroform and heated in a sealed tube at 80° C. for 46 hours. The resulting red precipitate was filtered and washed in turn with iced chloroform and ether to give 1,2,3,3-tetramethylindolenium iodide (2.4 g, 8.0 mmols) as a pale red powder (yield 76%).

EXAMPLE 5

Synthesis of 2-methylene-1,3,3-trimethylindoline 1,2,3,3-Tetramethylindolenium iodide (650 mg, 2.2 mmols) was added to 20 ml of an aqueous 1 mol/liter sodium hydroxide solution, which was stirred at room temperature for 30 minutes and a yellow oily substance on the liquid surface was extracted three times with 15 ml of ether. Then, the ether layer was washed with a saturated saline solution and dried over anhydrous sodium sulfate. The solvent was distilled under reduced pressure to give 2-methylene-1,3,3-trimethylindoline(360 mg, 2.1 mmols) as a pale yellow liquid (yield 94% ).

$^1$H-NMR(60 MHz, CDCl$_3$); δ 1.3(s, 6 H, CH$_3$), 3.0(s, 3 H, N-CH$_3$), 6.5~7.0 (dd, 2 H, vinyl), 7.0~7.2 (m, 4 H, ArH)

EXAMPLE 6

Synthesis of 8'-(trans)-benzamidecyclohexyl-carbonyloxymethyl- 6'-nitro-1,3,3-trimethylspiro[(2'H)-1'-benzopyran -2,2'-indoline]

To 2-methylene-1,3,3-trimethylindoline (170 mg, 1.0 mmol) was added 3-(trans)-benzamidecyclohexylcarbonyloxy-methyl -5-nitrosalicylaldehyde (430 mg, 1.0 mmol) dissolved in 20 ml of 2-butanone and stirred at room temperature under a dark place for 20 hours, and then the solvent was distilled of in a rotary evaporator to give 650 mg of a purple tarry substance. This tarry substance was purified by silica gel column chromatography to give a purple tarry substance (270 mg, 0.46 mmol, yield 48%). Further, a diastereomer ratio at this stage was 1:1 and a specific optical rotation at a mercury line of 435 nm was –128 degree (c=0.10, toluene).

MS(EI, 20eV); m/e=581(M$^+$). FT-IR(KBr, cm$^{-1}$); 2932~2857, 1736, 1649, 1605, 1532, 1332, 924, 744.

An absorption spectrum of a toluene solution of this compound (8.5×10$^{-4}$ mols/liter) was shown in FIG. 1.

EXAMPLE 7

Optical resolution of 8'-(trans)-benzamidecyclo-hexylcarbonyloxymethyl- 6'-nitro-1,3,3-trimethylspiro[(2'H)-1'-benzopyran-2,2'-indoline]

8'-(Trans)-benzamidecyclohexylcarbonyloxymethyl-6'-nitro -1,3,3-trimethylspiro[(2'H)-1'-benzopyran-2,2'-indoline](880 mg, 1.5 mmols) as a racemic modification was dissolved in 3 ml of ether containing 10 volume % methylene chloride at room temperature and the mixture was allowed to stand at room temperature for 69 hours to precipitate a crystal. A yellow crystal (602 mg, 1.0 mmol) was obtained by separating a mother liquor. The yield was 137% when the half amount thereof is taken as 100%. The specific optical rotation of the crystal was +230 degree (c=0.10, toluene). On the other hand, the mother liquor was concentrated to give 277 mg of a purple tarry substance. The specific optical rotation of the tarry substance was –120 degree. The optical purity of the resulting crystal described above can be further improved by washing with a small amount of a mixed solution of methylene chloride and ether. The optical purity of the crystal obtained after washing with the solvent was found to be (+)-modification:(–)-modification (=84:16) due to an integrated value of N-Me in $^1$H-NMR (400 MHz, C$_6$H$_6$) and the specific optical rotation at a mercury line of 435 nm was +612 degree (c=0.10, toluene).

$^1$H-NMR (400 MHz, C$_6$D$_6$) (+)-modification; δ 0.97 (s, 3 H, 3-Me), 1.23(s, 3 H, 3-Me), 1.38~2.21(m, 9 H, cyclohexane ring), 2.41 (s, 3 H, N-Me), 4.15(br, 1 H, cyclohexane ring), 4.63 (d, J=12.8 Hz, 1 H, 8'-CH$_2$), 4.74(d, J=12.8 Hz, 1 H, 8'-CH$_2$), 5.29(d, J=10.3 Hz, 1 H, 4'-H), 5.60(br, 1 H, NH), 6.07(d, J=10.4 Hz, 1 H, 3'-H), 6.38~8.00(m, 11H):

(–)-modification; δ 0.96 (s, 3 H, 3-Me), 1.16(s, 3 H, 3-Me), 1.38~2.2] (m, 9 H, cyclohexane ring), 2.51(s, 3 H, N-Me), 4.13(br, 1 H, cyclohexane ring), 4.65(d, J=12.8 Hz, 1 H, 8'-CH$_2$), 4.70(d, J=12.8 Hz, 1 H, 8'-CH$_2$), 5.28(d, J=10.3 Hz, 1 H, 4'-H), 5.60(br, 1 H, NH), 6.05(d, J=10.4 Hz, 1 H, 3'-H), 6.38~8.00(m, 11 H)

EXAMPLE 8

Optical resolution of 8'-(trans)-benzamidecyclo-hexylcarbonyloxymethyl- 6'-nitro-1,3,3-trimethylspiro[(2'H)-1'-benzopyran -2,2'-indoline]/PMMA cast film Immediately after 8'-(trans)-benzamidecyclohexyl-carbonyloxymethyl -6'-nitro-1,3,3-trimethylspiro[(2'H)-1'-benzopyran -2,2'-indoline] (44.8 mg) of which specific optical rotation at a mercury line of 435 nm is +240 degree (c=0.10, toluene) and polymethyl methacrylate (PMMA) (127.4 mg) were dissolved in 0.3 ml of dichloromethane at room temperature, the resulting solution was casted on a glass plate and dried in a vacuum line for 55 minutes. The optical purity of the present compound in the film obtained immediately after drying was found to be (+)-modification:(−)-modification (=2.20:1) due to an integrated value of N-Me in $^1$H-NMR (400 MHz, $C_6D_6$) of the part of the film. When this film was allowed to stand at room temperature under a dark place, slight epimerization was arisen at the beginning of the standing and the optical purity was deteriorated. However, the tendency of deterioration of the optical purity decreased with a lapse of time. After 100 hours, it became stable at a state wherein the optical purity is maintained at (+)-modification:(−)-modification (=1.83:1), and the optical purity did not change even after 360 hours. That is, optical activity of optically active spiropyran could be maintained stably in a PMMA cast film. Further, this state could be stably detected many times by measuring the specific optical rotation without deteriorating the optical purity. On the other hand, when this film was heated at 110° C. for 2 hours, the optical purity became (+)-modification:(−)-modification (=1:1) (epimer) and the optical activity was disappeared.

Industrial applicability

This is the first time that an optically active spiropyran compound has been isolated, according to the present invention. This compound exhibits optical rotation because it is an optically active substance. The spiropyran compound wherein an asymmetric center is introduced on a spirocarbon exhibits extremely large optical rotation. It is possible to develop optical materials such as high-density optical recording materials, optical filters, image forming materials, non-linear optical devices, writable high-density optical recording materials wherein non-destructive read-out has been accomplished, photosensitive materials, non-linear optical device and conversion of optical energy into dynamic energy, by utilizing physical properties obtained in the compound of the present invention for the first time, in addition to photochromism properties of spiropyran.

I claim:

1. A spiropyran compound represented by the formula (1):

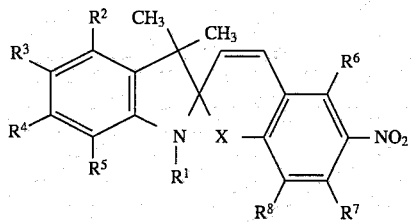

wherein $R^1$ is alkyl group having 1 to 20 carbon atoms, aralkyl group, hydroxyethyl group, methacryloxymethyl group or methacryloxyethyl group; $R^2$, $R^3$, $R^4$ and $R^5$ are the same or different and are each hydrogen atom, alkyl group having 1 to 6 carbon atoms, aryl group, aralkyl group, alkoxy group having 1 to 5 carbon atoms, hydroxymethyl group, carboxyl group, halogen atom, amino group, cyano group, trichloromethyl group, trifluoromethyl group or nitro group; $R^6$ and $R^7$ are the same or different and are each hydrogen atom, alkyl group having 1 to 6 carbon atoms, aryl group, aralkyl group, halogen atom, cyano group or nitro group; $R^8$ is alkyl group having 1 to 6 carbon atoms, hydroxymethyl group, carboxyl group, methoxycarbonyl group, methacryloxymethyl group or vinyl group; at least one of $R^1$ to $R^8$ is substituted with a substituent having properties as a reagent for optical resolution; and X is oxygen atom or sulfur atom.

2. An optically active spiropyran compound wherein an asymmetric center is introduced on a spirocarbon, which is represented by the formula (2):

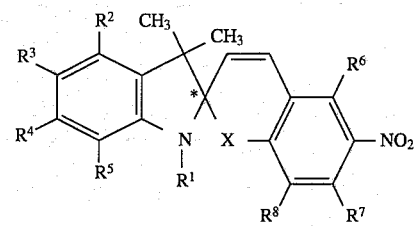

wherein $R^1$ is alkyl group having 1 to 20 carbon atoms, aralkyl group, hydroxyethyl group, methacryloxymethyl group or methacryloxyethyl group; $R^2$, $R^3$, $R^4$ and $R^5$ are the same or different and are each hydrogen atom, alkyl group having 1 to 6 carbon atoms, aryl group, aralkyl group, alkoxy group having 1 to 5 carbon atoms, hydroxymethyl group, carboxyl group, halogen atom, amino group, cyano group, trichloromethyl group, trifluoromethyl group or nitro group; $R^6$ and $R^7$ are the same or different and are each hydrogen atom, alkyl group having 1 to 6 carbon atoms, aryl group, aralkyl group, halogen atom, cyano group or nitro group; $R^8$ is alkyl group having 1 to 6 carbon atoms, hydroxymethyl group, carboxyl group, methoxycarbonyl group, methacryloxymethyl group or vinyl group; at least one of $R^1$ to $R^8$ is substituted with a substituent having properties as a reagent for optical resolution; and X is oxygen atom or sulfur atom.

3. A compound as defined in claim 1 or 2 wherein $R^1$ is methyl group, ethyl group, propyl group, octadecyl group, hydroxyethyl group, methacryloxymethyl group or methacryloxyethyl group; $R^2$ is hydrogen atom; $R^3$ and $R^5$ are the same or different and indicate hydrogen atom, methyl group, methoxy group, chlorine atom, bromine atom, amino group, dimethylamino group, diethylamino group or nitro group; $R^4$ is hydrogen atom, methyl group of methoxy group; $R^6$ and $R^7$ indicate hydrogen atom; $R^8$ is hydrogen atom, hydroxymethyl group, carboxyl group, vinyl group or methacryloxymethyl group; at least one of $R^1$, $R^3$, $R^5$ and $R^8$ is substituted with a group having properties as a reagent for optical resolution; and X is oxygen atom of sulfur atom.

4. A compound as defined in claim 1 or 2 wherein the group having properties as a reagent for optical resolution is at least one group selected from among a group derived from optically active substance reacting with an alcoholic hydroxyl group, optically active substance reacting with a carboxyl group and optically active substance reacting with an amino group.

5. A compound as defined in claim 1 or 2 wherein the reagent for optical resolution is at least one reagent selected from among (+)- and (−)-(trans)-2-benzamidecyclohexyl-carboxylic acid, (+)- and (−)-(cis)-2-benzamidecyclohexyl-carboxylic acid, (+)- and (−)-1-phenylethanesulfonic acid, (+)- and (−)-mandelic acid, (+)- and (−)-tartaric acid, (+)- and (−)-malic acid, (+)- and (−)-camphoric acid, (+)- and (−)-camphorsulfonic acid, (+)- and (−)-pylrolidonecarboxylic acid, (+)- and (−)-aspartic acid, (+)- and (−)-α-methylbenzylamine, (+)- and (−)-1-(1-naphthyl) ethylamine, (+)- and (−)-1-phenyl-2-(p-tolyl)ethylamine, (+)- and (−)-ephedrine, (+)- and (−)-lysine and (+)- and (−)-arginine.

6. An optical functional material containing the spiropyran compound of the formula (1)

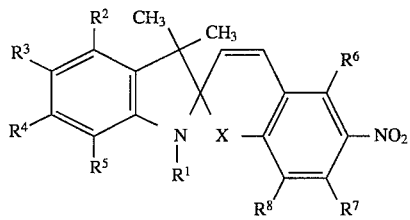

wherein $R^1$ is alkyl group having 1 to 20 carbon atoms, aralkyl group, hydroxyethyl group, methacryloxymethyl group or methacryloxyethyl group; $R^2$, $R^3$, $R^4$ and $R^5$ are the same or different and are each hydrogen atom, alkyl group having 1 to 6 carbon atoms, aryl group, aralkyl group, alkoxy group having 1 to 5 carbon atoms, hydroxymethyl group, carboxyl group, halogen atom, amino group, cyano group, trichloromethyl group, trifluoromethyl group or nitro group; $R^6$ and $R^7$ are the same or different and are each hydrogen atom, alkyl group having 1 to 6 carbon atoms, aryl group, aralkyl group, halogen atom, cyano group or nitro group; $R^8$ is alkyl group having 1 to 6 carbon atoms, hydroxymethyl group, carboxyl group, methoxycarbonyl group, methacryloxymethyl group or vinyl group; at least one of $R^1$ to $R^8$ is substituted with a substituent having properties as a reagent for optical resolution; and X is oxygen atom or sulfur atom., or formula (2)

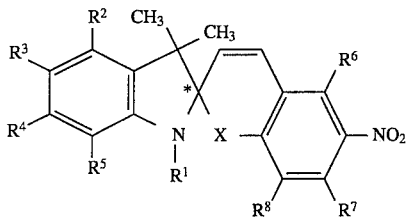

wherein $R^1$ is alkyl group having 1 to 20 carbon atoms, aralkylgroup, hydroxyethyl group, methacryloxymethyl group or methacryloxyethyl group; $R^2$, $R^3$, $R^4$ and $R^5$ are the same or different and are each hydrogen atom, alkyl group having 1 to 6 carbon atoms, aryl group, aralkyl group, alkoxy group having 1 to 5 carbon atoms, hydroxymethyl group, carboxyl group, halogen atom, amino group, cyano group, trichloromethyl group, trifluoromethyl group or nitro group; $R^6$ and $R^7$ are the same or different and are each hydrogen atom, alkyl group having 1 to 6 carbon atoms, aryl group, aralkyl group, halogen atom, cyano group or nitro group; $R^8$ is alkyl group having 1 to 6 carbon atoms, hydroxymethyl group, carboxyl group, methoxycarbonyl group, methacryloxymethyl group or vinyl group; at least one of $R^1$ to $R^8$ is substituted with a substituent having properties as a reagent for optical resolution; and X is oxygen atom or sulfur atom.

7. An optical functional material made from a molding material of a mixture of the spiropyran compound of the formula (1)

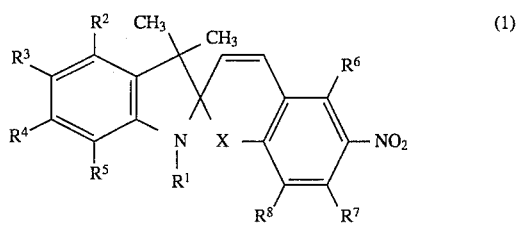

wherein $R^1$ is alkyl group having 1 to 20 carbon atoms, aralkyl group, hydroxyethyl group, methacryloxymethyl group or methacryloxyethyl group; $R^2$, $R^3$, $R^4$ and $R^5$ are the same or different and are each hydrogen atom, alkyl group having 1 to 6 carbon atoms, aryl group, aralkyl group, alkoxy group having 1 to 5 carbon atoms, hydroxymethyl group, carboxyl group, halogen atom, amino group, cyano group, trichloromethyl group, trifluoromethyl group or nitro group; $R^6$ and $R^7$ are the same or different and are each hydrogen atom, alkyl group having 1 to 6 carbon atoms, aryl group, aralkyl group, halogen atom, cyano group or nitro group; $R^8$ is alkyl group having 1 to 6 carbon atoms, hydroxymethyl group, carboxyl group, methoxycarbonyl group, methacryloxymethyl group or vinyl group; at least one of $R^1$ to $R^8$ is substituted with a substituent having properties as a reagent for optical resolution; and X is oxygen atom or sulfur atom, or formula (2)

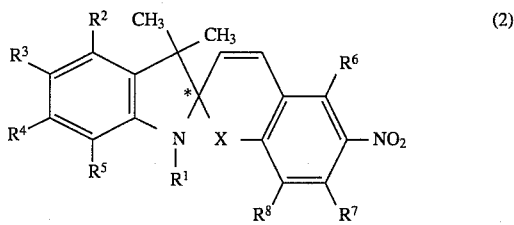

wherein $R^1$ is alkyl group having 1 to 20 carbon atoms, aralkyl group, hydroethyl group, methacryloxymethyl group or methacryloxyethyl group; $R^2$, $R^3$, $R^4$ and $R^5$ are the same or different and are each hydrogen atom, alkyl group having 1 to 6 carbon atoms, aryl-group, aralkyl group, alkoxy group having 1 to 5 carbon atoms, hydroxymethyl group, carboxyl group, halogen atom, amino group, cyano group, trichloromethyl group, trifluoromethyl group or nitro group; $R^6$ and $R^7$ are the same or different and are each hydrogen atom, alkyl group having 1 to 6 carbon atoms, aryl group, aralkyl group, halogen atom, cyano group or nitro group; $R^8$ is alkyl group having 1 to 6 carbon atoms, hydroxymethyl group, carboxyl group, methoxycarbonyl group, methacryloxymethyl group or vinyl group; at least one of $R^1$ to $R^8$ is substituted with a substituent having properties as a reagent for optical resolution; and X is oxygen atom or sulfur atom, and a resin.

8. An optical functional material made from a homopolymer of the spiropyran compound of the formula (1)

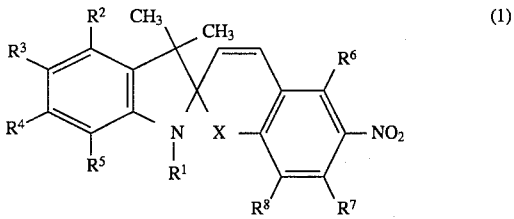

wherein $R^1$ is alkyl group having 1 to 20 carbon atoms, aralkyl group, hydroxyethyl group, methacryloxymethyl group or methacryloxyethyl group; $R^2$, $R^3$, $R^4$ and $R^5$ are the same or different and are each hydrogen atom, alkyl group having 1 to 6 carbon atoms, aryl group, aralkyl group, alkoxy group having 1 to 5 carbon atoms, hydroxymethyl group, carboxyl group, halogen atom, amino group, cyano group, trichloromethyl group, trifluoromethyl group or nitro group; $R^6$ and $R^7$ are the same or different and are each hydrogen atom, alkyl group having 1 to 6 carbon atoms, aryl group, aralkyl group, halogen atom, cyano group or nitro group; $R^8$ is alkyl group having 1 to 6 carbon atoms, hydroxymethyl group, carboxyl group, methoxycarbonyl group, methacryloxymethyl group or vinyl group; at least one of $R^1$ to $R^8$ is substituted with a substituent having properties as a reagent for optical resolution; at least one of $R^1$ and $R^8$ contains an ethylenically unsaturated double bond; and X is oxygen atom or sulfur atom, or formula (2)

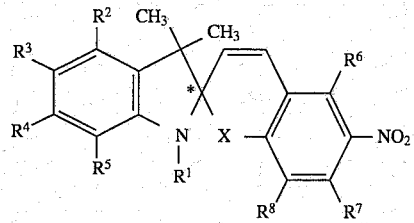

(2)

wherein $R^1$ is alkyl group having 1 to 20 carbon atoms, aralkyl group, hydroxyethyl group, methacryloxymethyl group or methacryloxyethyl group; $R^2$, $R^3$, $R^4$ and $R^5$ are the same or different and are each hydrogen atom, alkyl group having 1 to 6 carbon atoms, aryl group, aralkyl group, alkoxy group having 1 to 5 carbon atoms, hydroxymethyl group, carboxyl group, halogen atom, amino group, cyano group, trichloromethyl group, trifluoromethyl group or nitro group; $R^6$ and $R^7$ are the same or different and are each hydrogen atom, alkyl group having 1 to 6 carbon atoms, aryl group, aralkyl group, halogen atom, cyano group or nitro group; $R^8$ is alkyl group having 1 to 6 carbon atoms, hydroxymethyl group, carboxyl group, methoxycarbonyl group, methacryloxymethyl group or vinyl group; at least one of $R^1$ to $R^8$ is substituted with a substituent having properties as a reagent for optical resolution; at least one of $R^1$ and $R^8$ contains an ethylenically unsaturated double bond; and X is oxygen atom or sulfur atom.

9. An optical functional material made from a copolymer of the spiropyran compound of the formula (1)

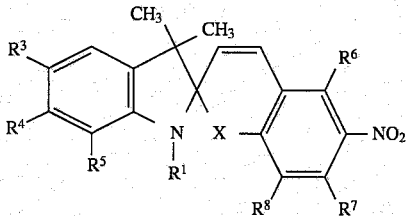

(1)

wherein $R^1$ is alkyl group having 1 to 20 carbon atoms, aralkyl group, hydroxyethyl group, methacryloxymethyl group or methacryloxyethyl group; $R^2$, $R^3$, $R^4$ and $R^5$ are the same or different and are each hydrogen atom, alkyl group having 1 to 6 carbon atoms, aryl group, aralkyl group, alkoxy group having 1 to 5 carbon atoms, hydroxymethyl group, carboxyl group, halogen atom, amino group, cyano group, trichloromethyl group, trifluoromethyl group or nitro group; $R^6$ and $R^7$ are the same or different and are each hydrogen atom, alkyl group having 1 to 6 carbon atoms, aryl group, aralkyl group, halogen atom, cyano group or nitro group; $R^8$ is alkyl group having 1 to 6 carbon atoms, hydroxymethyl group, carboxyl group, methoxycarbonyl group, methacryloxymethyl group or vinyl group; at least one of $R^1$ to $R^8$ is substituted with a substituent having properties as a reagent for optical resolution; at least one of $R^1$ and $R^8$ contains an ethylenically unsaturated double bond; and X is oxygen atom or sulfur atom, or formula (2)

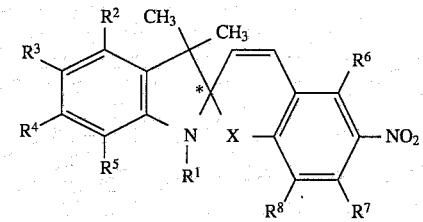

(2)

wherein $R^1$ is alkyl group having 1 to 20 carbon atoms, aralkyl group, hydroxyethyl group, methacryloxymethyl group or methacryloxyethyl group; $R^2$, $R^3$, $R^4$ and $R^5$ are the same or different and are each hydrogen atom, alkyl group having 1 to 6 carbon atoms, aryl group, aralkyl group, alkoxy group having 1 to 5 carbon atoms, hydroxymethyl group, carboxyl group, halogen atom, amino group, cyano group, trichloromethyl group, trifluoromethyl group or nitro group; $R^6$ and $R^7$ are the same or different and are each hydrogen atom, alkyl group having 1 to 6 carbon atoms, aryl group, aralkyl group, halogen atom, cyano group or nitro group; $R^8$ is alkyl group having 1 to 6 carbon atoms, hydroxymethyl group, carboxyl group, methoxycarbonyl group, methacryloxymethyl group or vinyl group; at least one of $R^1$ to $R^8$ is substituted with a substituent having properties as a reagent for optical resolution; at least one of $R^1$ and $R^8$ contains an ethylenically unsaturated double bond; and X is oxygen atom or sulfur atom, and other copolymerizable monomer.

* * * * *